United States Patent [19]
Gard et al.

[11] Patent Number: 5,090,039
[45] Date of Patent: Feb. 18, 1992

[54] INSPECTING COILED TUBING FOR WELL OPERATIONS

[75] Inventors: Michael F. Gard; Eric S. Pasternack, both of Plano; Lonnie J. Smith, Allen, all of Tex.

[73] Assignee: Atlantic Richfield Company, Los Angeles, Calif.

[21] Appl. No.: 163,332

[22] Filed: Mar. 2, 1988

[51] Int. Cl.⁵ .................................... G01N 23/02
[52] U.S. Cl. ............................... 378/59; 378/58; 250/268
[58] Field of Search ............... 378/51, 58, 59, 62; 250/268, 359, 59.1

[56] References Cited

U.S. PATENT DOCUMENTS

| | | | |
|---|---|---|---|
| 3,012,145 | 12/1961 | Erion et al. | 250/268 |
| 3,178,576 | 4/1965 | Arvanetakis | 378/59 |
| 3,628,029 | 12/1971 | Tompkins | 378/59 |
| 4,187,425 | 1/1980 | Thompson | 378/59 |
| 4,695,729 | 9/1987 | Monno et al. | 378/59 |
| 4,725,963 | 2/1988 | Taylor et al. | 378/58 |

FOREIGN PATENT DOCUMENTS 0216705 4/1987 European Pat. Off. ............ 378/58

Primary Examiner—Janice A. Howell
Assistant Examiner—David P. Porta
Attorney, Agent, or Firm—Michael E. Martin

[57] ABSTRACT

A coiled tubing injection unit for injecting a continuous length of coiled steel tubing into a wellbore for performing well operations includes an x-ray inspection apparatus arranged to continuously monitor the wall section of the tubing as it is inserted into or withdrawn from the well to detect structural defects in the tubing. An x-ray source and detector unit are mounted in a housing which is supported for rotation about the longitudinal axis of the tubing for projecting an x-ray image through suitable processing and display apparatus. The x-ray detection unit may be mounted on a level wind mechanism of the coiled tubing storgage spool or at another point between the storage spool and the wellhead into which the tubing is being injected.

1 Claim, 2 Drawing Sheets

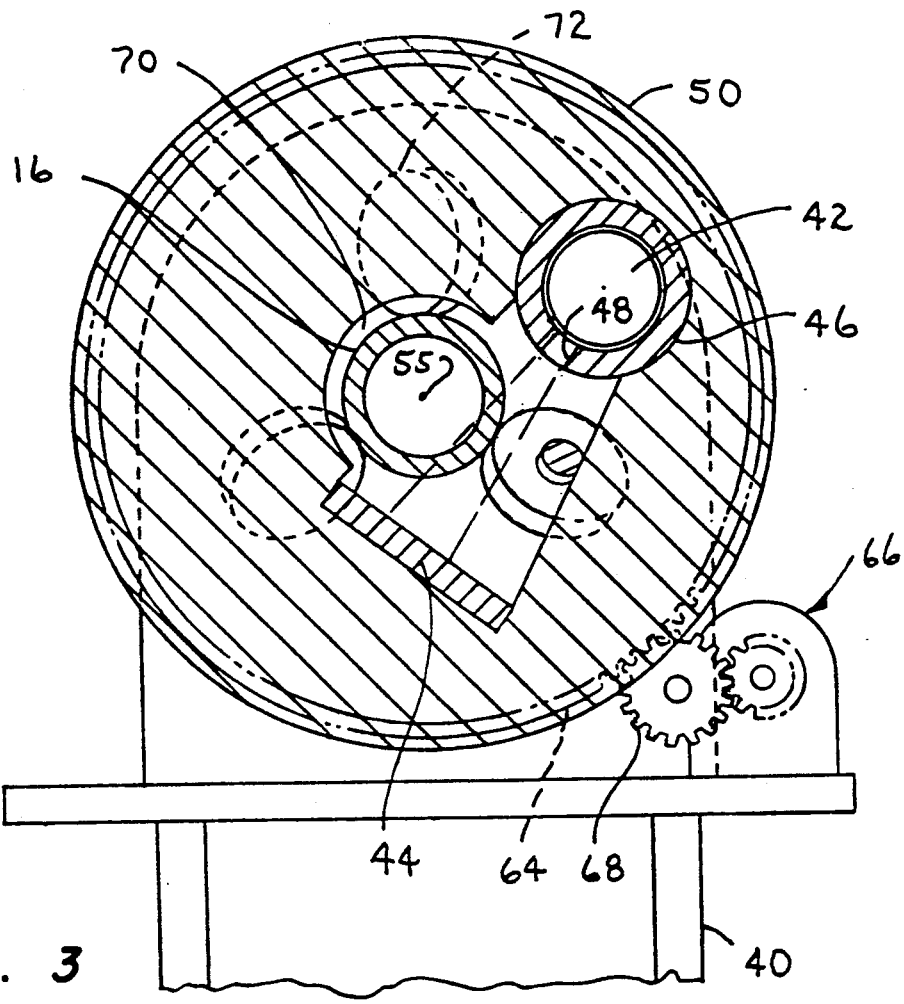
FIG. 3
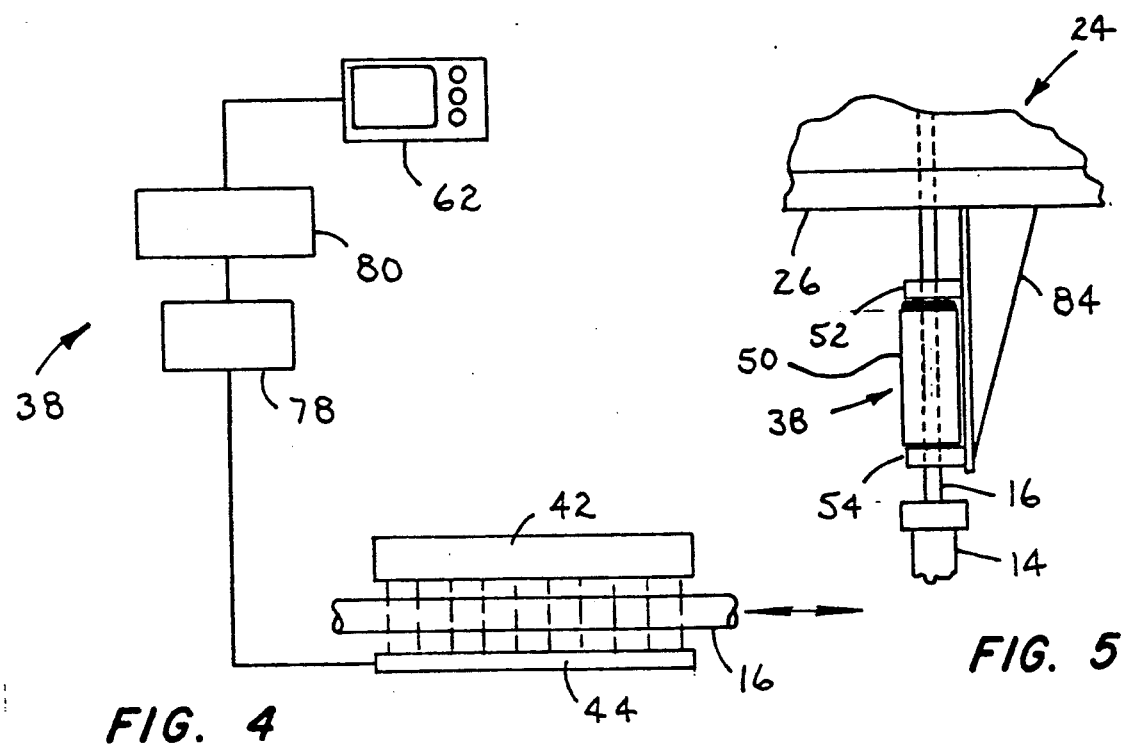
FIG. 4
FIG. 5

INSPECTING COILED TUBING FOR WELL OPERATIONS

BACKGROUND OF THE INVENTION

1. Field of the Invention

The present invention pertains to an apparatus and method for x-ray imaging coilable tubing used for injection into subterranean wells for inspecting the integrity of the tubing.

2. Background

An increasingly popular method of performing well operations comprises extending continuous lengths of relatively thinwalled steel tubing into the wellbore for the injection of fluids, well cleanout operations and the insertion and withdrawal of certain wellbore tools. An advantage of utilizing such tubing is that the tubing may be stored on a reel in a continuous length similar to a cable and the tubing is, of course, capable of conducting fluids into and out of the wellbore and serving as a sheath or shield for electrical conductors.

However, since the tubing undergoes plastic deformation with each dereeling, injection, withdrawal and re-reeling operation, it is important to monitor the onset of fatigue cracking or the detection of any other defect in the structure of the tubing. In this respect, prior art efforts to inspect coilable tubing has required complete dereeling of the tubing from its storage spool while passing the tubing through conventional inspection equipment. This process is time consuming and since the tubing must be re-reeled and then dereeled again during use, a fatigue crack may develop after the inspection process, but at an early time during subsequent use. In this regard, it has been considered highly desirable to be able to inspect coiled tubing before injection into the wellbore, during each injection operation or during withdrawal of the tubing after each use thereof. In this way, the risk of catastrophic failure of the tubing while it is in the wellbore is minimized and early detection of fatigue cracks or fissures which may result in tube failure or at least provide a fluid leakage flow path which could seriously damage or impair well operations is provided.

The present invention is directed to providing a method and apparatus for substantially continuous inspection of coiled tubing at the wellsite both before and after use of the tubing for injection into a wellbore.

SUMMARY OF THE INVENTION

The present invention provides an improved apparatus and method for inspection of coilable tubing, particularly of the type utilized for subterranean well operations.

In accordance with one aspect of the present invention, a coiled tubing inspection apparatus is provided which is operable to inspect the circumferential wall of the tubing without requiring interruption of operations in reeling or dereeling the tubing during its normal use. In accordance with another aspect of the invention, a coiled tubing inspection apparatus is provided which utilizes x-ray imaging and does not require physical contact of the sensing devices of the inspection apparatus with the tubing.

The present invention still further provides a coiled tubing inspection device which is operable with nonmagnetic tubing material and may be mounted for inspecting the tubing before being reeled onto a storage spool or while being dereeled from the storage spool and prior to injection of the tubing into a wellbore.

The present invention still further provides a unique apparatus which is adapted to be mounted with respect to a coiled tubing injection unit such that the coiled tubing may be inspected substantially continuously without interrupting tubing injection or withdrawal operations and without requiring rotation of the tubing about its own axis during the inspection process. By using an x-ray imaging system which is movable relative to the tubing about the tubing longitudinal axis, the tubing may be continuously inspected both before and after its use without adversely affecting tubing installation or withdrawal operations.

Those skilled in the art will recognize the above described features and advantages of the present invention as well as other superior aspects thereof upon reading the detailed description which follows in conjunction with the drawing.

BRIEF DESCRIPTION OF THE DRAWING

FIG. 3 is a transverse view showing certain features of the tubing inspection apparatus;

FIG. 4 is a schematic diagram of the major components of the x-ray inspection apparatus of the present invention; and FIG. 5 is a detail view illustrating an alternate location of the inspection apparatus on the tubing injection unit.

DESCRIPTION OF PREFERRED EMBODIMENTS

Figure 1:
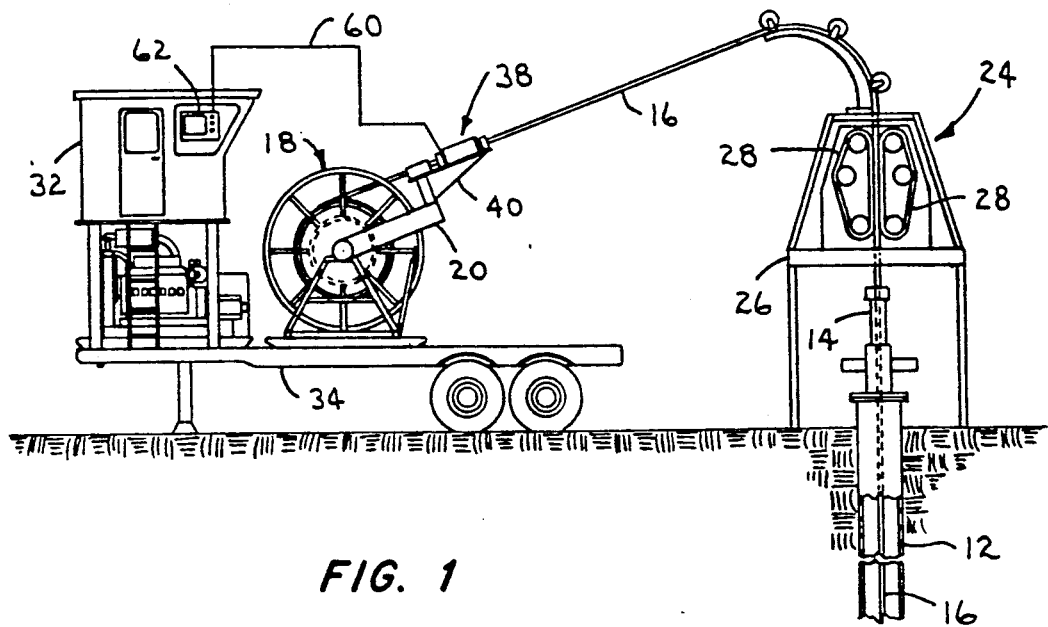
FIG. 1 is a view in somewhat schematic form of a coiled tubing injection unit in operation for injecting and withdrawing coilable tubing with respect to a wellbore and including the improved inspection method and apparatus of the present invention.

In the description which follows, like parts are marked throughout the specification and drawing with the same reference numerals, respectively. The drawing figures are not necessarily to scale and certain features are shown in schematic or somewhat generalized form in the interest of clarity and conciseness.

Referring now to FIG. 1, there is illustrated a wellbore having a conventional casing structure 12 and a wellhead 14 adapted for injection and withdrawal of elongated relatively thin walled steel tubing 16. The tubing 16 is typically of stainless or high strength low alloy steel, is formed in one continuous length of up to several thousand feet and is adapted to be stored on a rotatable spool or reel generally designated by the numeral 18. The spool 18 preferably includes a so-called level wind mechanism 20 which provides for continuously reeling and unreeling the tubing 16 with respect to the spool in a uniform manner. The level wind mechanism 20 typically includes a fairlead 22 for guiding the tubing 16 onto and off of the spool 18.

The tubing 16 is injected into and withdrawn from the casing 12 by a tubing injection unit 24 which may be of a type commercially available. The tubing injection unit 24 is suitably mounted above the wellhead 14 on a portable support structure 26 and typically includes a pair of opposed endless chains 28 which are driven in timed relationship and include suitable means, not shown, for gripping the tubing 16 to forcibly inject or withdraw the tubing with respect to the casing 12 in accordance with the direction of traversal of the chains. A swivelable guide member 30 is mounted on the tubing injection unit 24 for assistance in changing the directional course of the tubing 16 between the spool 18 and the injection unit 24. Operation of the injection unit 24 may be carried out by remote control from an operator's cab 32 suitably mounted on a semi-trailer 34, which also supports the spool 18. By way of example, a commercially available tubing injection unit which is suitable for use with the present invention is a type available from Dowell-Schlumberger, Inc., Houston, Tex. and generally known as a coiled tubing unit. Similar units are commercially available under the trademark Bowen and by Rebound Rig Company, Ltd., Brooks, Alberta, Canada.

The tubing 16 is typically provided as either stainless or high strength low alloy seamless steel tubing having an outside diameter ranging from about 0.75 inches to 1.50 inches with a wall thickness of about 0.063 inches to 0.134 inches. The tubing, of course, undergoes plastic deformation as it is reeled onto and off of the spool 18 with each injection and withdrawal operation. Moreover, the tubing 16 is also subjected during operation to high axial tension and compression stresses during withdrawal and injection operations and is subjected to the corrosive effects of wellbore fluids and fluids which are being injected into the wellbore through the tubing. In this respect, it is important to be able to at least periodically, and preferably substantially continuously, monitor the structural integrity of the tubing by inspecting the tubing for the onset of flexural or stress related cracks or defects in the tubing wall. The metallurgy of the tubing 16 may or may not prevent effective inspection processes utilizing magnetic flux measurement. Moreover, ultrasonic inspection techniques are considered difficult to accomplish on a continuous basis because of the need to provide an acoustic coupling medium for transmitting the acoustic signal between a sending and receiving unit and the surface of the tubing itself. Still further, complications in regard to inspection of the tubing arise due to the problem not being able to rotate the tubing with respect to an inspection device without interrupting the operation of the tubing or substantially modifying the tubing injection and storage equipment.

However, in accordance with the present invention it is contemplated to utilize radiographic imaging of the tubing wall as the tubing 16 is wound onto or off of the spool 18. In accordance with the present invention it is contemplated that inspection of the tubing 16 for defects in the tubing wall should be carried out at a point before the injection unit 24 operates to insert the tubing into the wellbore so that the injection unit may be stopped from injecting the tubing before a substantial load is placed on the tubing at a point where failure will cause the greatest damage or inconvenience, namely between the injection unit and the wellbore itself. Accordingly, the present invention contemplates the placement of a tubing inspection apparatus in one preferred location which is between the injection unit 24 and the spool 18.

Figure 2:
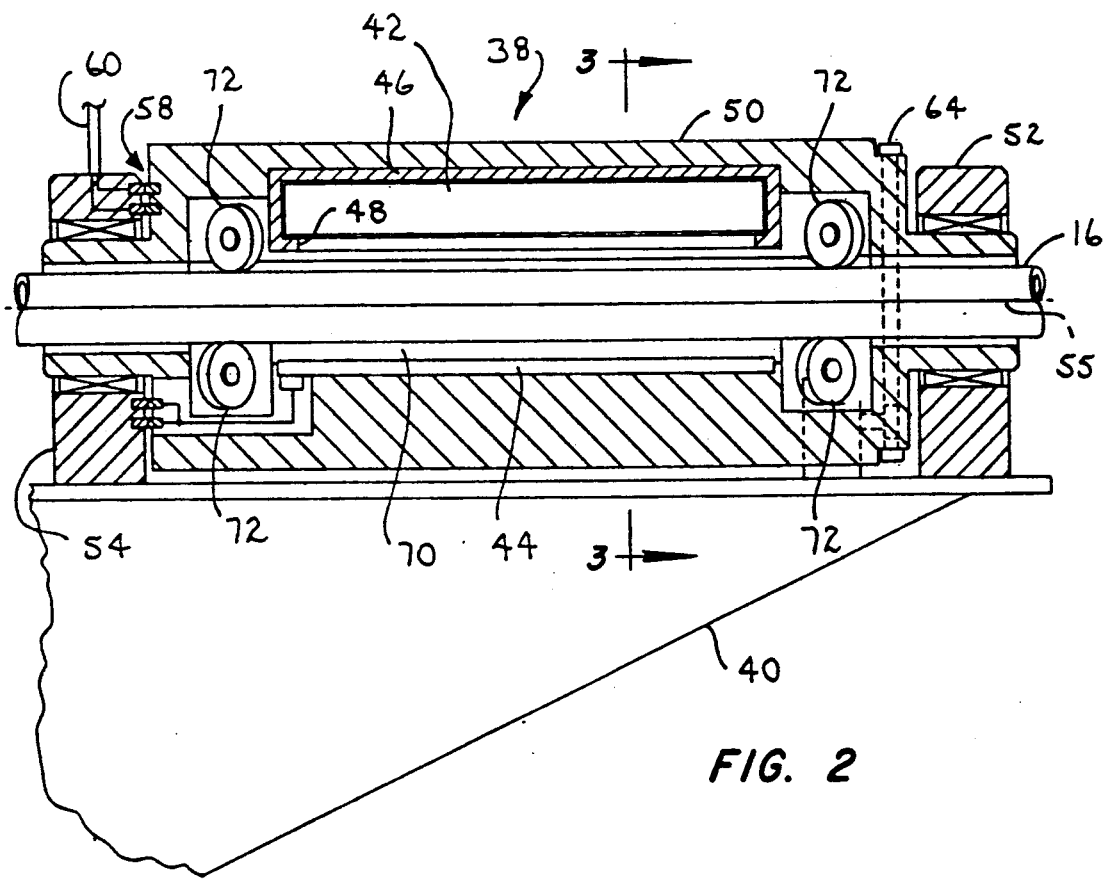
FIG. 2 is a longitudinal central section view illustrating one preferred embodiment of the tubing inspection apparatus.

As illustrated in FIG. 1, a tubing inspection apparatus, generally designated by the numeral 38 is disposed on the level wind mechanism 20 between the fairlead 22 and the tubing injection unit 24. The apparatus 38 is supported by a support bracket 40 and is disposed around the tubing 16 in such a way that the full circumference of the tubing may be inspected continuously and without actual physical contact of the tubing by the inspection sensing components. Referring now primarily to FIGS. 2 and 3, the tubing inspection apparatus 38 preferably comprises radiographic means including an electromagnetic radiation source and detection device including a source of electromagnetic radiation in the x-ray spectrum, generally designated by the numeral 42, and a radiation detector unit 44. The radiation source 42 may be an x-ray emitting tube or, preferably, a quantity of a radionuclide mounted in a suitable shield and collimator 46. The collimator 46 includes a suitable slot 48, FIG. 3 which permits the emission of x-rays which are projected through the wall of the tubing 16 and onto the detection unit 44. The detection unit 44 may be of a type similar to a type commercially available comprising a linear array of solid state x-ray image sensors, which are essentially photodiodes arranged in a linear array having a pitch as low as 0.45 mm and having a sensitive length of about 460 mm for an array of 1024 sensors. Commercially available detector units such as made by Thomson Electron Tubes and Devices, Dover, N.J. are capable of responding to x-ray energy in the range of 5 keV to 200 keV. One or more detector units 44 and x-ray sources 42 may be employed depending on the processing speed required for the inspection of the tubing 16.

The x-ray source 42 and the detector unit 44 may be adapted for support in a generally cylindrical housing 50, FIGS. 2 and 3, suitably mounted for rotation on the support 40 in spaced apart bearing mounts 52 and 54. The housing 50 may be constructed of two longitudinal sections, not shown, which are separable for removal from the tubing 16. The housing 50 is adapted to support the x-ray source 42 and the detector unit 44 offset from the tubing longitudinal central axis 55, as indicated in FIG. 3, so that the wall section of the tubing 16 may be continuously imaged for inspection purposes by rotating the housing 50 substantially continuously about the periphery of the tube 16. The signals representing the output from the detector unit 44 may be conducted through a slipring assembly 58 of suitable construction for transmitting signals to a cable 60 for transmission to further signal processing and displaying equipment to be described in general hereinbelow. The signals from one or more detector units 44 may also be utilized to produce cross-sectional radiographic images. Preferably a display unit 62 is mounted in the operator cab 32, see FIG. 1, for continuous display of the x-ray image of the tubing wall as it is inspected. As shown in FIGS. 2 and 3, the housing 50 is provided with suitable means for rotating the housing such as a gear 64 mounted thereon and suitably driven by a gearmotor 66 including a drive pinion 68 meshed with the gear 64.

The tubing 16 is required to be relatively precisely guided as it traverses through the interior space 70 of the housing 50 by a plurality of guide rollers 72 which are suitably mounted in the housing 50 spaced apart about the circumference of the tubing 16 and engaged therewith in sets of three rollers each as indicated in FIGS. 2 and 3. The rollers 72 are preferably mounted for rotation about axes which are somewhat skewed with respect to the axis 55 since the housing 50 is rotated while the tubing 16 is longitudinally traversed through the housing 50 during inspection operations. The tubing 16 may be continuously inspected as it is dereeled from or wound onto the spool 18 during tubing injection or withdrawal operations.

Referring briefly to FIG. 4, the tubing inspection apparatus 38 also includes a suitable signal processing unit 78 and a memory unit 80 for recalling certain images of the tubing as it is being continuously inspected. The memory unit 80 may be suitably controlled in timed relationship to the movement of the tubing 16 longitudinally through the detection apparatus so that a particular point on the tubing 16 may be recalled for further inspection or for repair.

Referring briefly also to FIG. 5, an alternate arrangement of the tubing inspection apparatus 38 is illustrated wherein the apparatus is mounted on a support member 84 which is connected to the frame 26 of the tubing injection unit 24 in such a way that the inspection apparatus 38 is adapted to inspect the tubing 16 at a point between the wellhead 14 and the tubing injection unit 24. This location of the tubing inspection apparatus 38 may be preferred in some applications so that the tubing may be inspected while it is under stress from injection or withdrawal forces. Close monitoring of the tubing during these operations may enable an operator to prevent catastrophic failure of the tubing which might develop from a crack which would occur as the tubing was being subjected to the stresses of injection or withdrawal operations.

Operation of the tubing inspection apparatus 38 is believed to be readily understandable from the foregoing description. The specific configuration of the radiation source illustrated may be modified to include sources requiring electrical energy input although the voltage magnitude which must be input to x-ray generating devices known in the art could present some problems in transmitting suitable energy to the housing 50 through conventional slipring assemblies or the like. In this respect, it is contemplated that a radiation source such as a radionuclide substance with a suitable collimator for directing the radiation beam toward the emitter slot and through the tubing wall is preferred. The number and specific arrangement and configuration of the x-ray detector units as well as the signal handling and conditioning equipment is believed to be within the purview of one of skill in the art of x-ray equipment.

Although a preferred embodiment of an improved method and apparatus for inspecting coiled tubing for use in well operations has been described hereinabove those skilled in the art will recognize that various substitutions and modifications may be made to the invention without departing from the scope and spirit of the appended claims.

What is claimed is:

1. In a coiled tubing system for insertion of a substantially continuous bendable length of metal tubing into and withdrawal from a wellbore, said system including a tubing injection unit disposed for injecting said length of tubing into said wellbore and storage means for dispensing said length of tubing and receiving said length of tubing from said injection unit, the improvement characterized by:

tubing inspection apparatus for substantially continuously inspecting the wall section of said tubing to detect cracks and structural defects which may lead to tubing failure, said apparatus comprising:

a source of electromagnetic radiation mounted in proximity to said tubing between said injection unit and a wellhead into which said tubing is injected;

a radiation detector unit for receiving signals from said source which have been projected through the wall of said tubing;

means for receiving signals from said detector unit for monitoring the structural integrity of the wall of said tubing during one of injecting and withdrawing said tubing with respect to said wellhead; and housing means supported for rotation about a longitudinal axis of said tubing, said source of radiation and said detector unit being mounted on said housing means for rotation therewith about the circumference of said tubing in such a way that said tubing is longitudinally extended through said housing means while said source of radiation and said detector unit are rotated to scan the wall of said tubing about substantially the entire circumference of said tubing during said one of injection and withdrawal of said tubing with respect to said wellhead so that said tubing is inspected while under one of compressive or tensile stress associated with said one of injection and withdrawal of said tubing with respect to said wellhead.

* * * * *